(12) United States Patent
Pitt et al.

(10) Patent No.: US 6,482,975 B1
(45) Date of Patent: Nov. 19, 2002

(54) BIS-POLY(ETHYLENE OXIDE) SURFACTANTS AND THEIR USE AS ANTISTATS IN PHOTOGRAPHIC MATERIALS

(75) Inventors: Alan R. Pitt, St Albans (GB); Trevor J. Wear, Harrow (GB)

(73) Assignee: Eastman Kodak Company, Rochester, NY (US)

( * ) Notice: Subject to any disclaimer, the term of this patent is extended or adjusted under 35 U.S.C. 154(b) by 0 days.

(21) Appl. No.: 09/857,877

(22) PCT Filed: Dec. 14, 1999

(86) PCT No.: PCT/GB99/04252

§ 371 (c)(1),
(2), (4) Date: Jun. 12, 2001

(87) PCT Pub. No.: WO00/37440

PCT Pub. Date: Jun. 29, 2000

(30) Foreign Application Priority Data

Dec. 19, 1998 (GB) .............................................. 9827982

(51) Int. Cl.$^7$ .............................................. C07C 69/34
(52) U.S. Cl. ...................................... 560/198; 560/199
(58) Field of Search ................................... 560/198, 199

(56) References Cited

U.S. PATENT DOCUMENTS

| 4,582,781 A | 4/1986 | Chen et al. |
| 4,610,955 A | 9/1986 | Chen et al. |
| 5,510,513 A | 4/1996 | Kai et al. |
| 5,650,158 A | * 7/1997 | Eierdanz et al. |

FOREIGN PATENT DOCUMENTS

| DE | 4238032 A1 | 5/1994 |
| EP | 619293 A1 | 12/1994 |

* cited by examiner

Primary Examiner—Alan L. Rotman
Assistant Examiner—Hector Reyes
(74) Attorney, Agent, or Firm—Doreen M. Wells

(57) ABSTRACT

Optionally fluorine-substituted alkyl or alkenyl poly (ethylene oxides) the compounds of the general formula

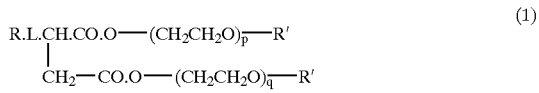

in which R is an alkyl group with 10–20 carbon atoms, an alkenyl group with 10–20 carbon atoms or a fluoroalkyl or fluoro-alkenyl group with f carbon atoms that each bear at least one fluorine atom and g carbon atoms that bear only hydrogen atoms, in which 1.5 f+g=10–20 and g may optionally be zero.

R' is an alkyl group with 1 to 4 carbon atoms,

L is a linking group, a linking atom or a chemical bond, and p is at least 2, q is at least 2 and p+q=from 4 to 100, may be prepared by reacting maleic anhydride with a poly(ethylene glycol) alkyl. ether and reacting the resultant intermediate product with a compound of the formula RL'H in which L' is a linking group or linking atom. Compounds of the formula (1) may also be prepared by reacting RL-substituted succinic anhydrides with a alkyl end-capped polyethylene glycol. The compounds of the formula (1) exhibit good solubility and surface activity and may be used as antistats, particularly in gelatin media, optionally in conjunction with lithium triflate or the like, in photographic coatings.

32 Claims, No Drawings

BIS-POLY(ETHYLENE OXIDE) SURFACTANTS AND THEIR USE AS ANTISTATS IN PHOTOGRAPHIC MATERIALS

FIELD OF THE INVENTION

The present invention relates to novel bis-poly(ethylene oxide) oligomeric surfactants, to a process for their production and to their use as antistats for photographic coatings.

BACKGROUND OF THE INVENTION

It is known in the art to include a surfactant in photographic coatings in order to impart antistatic properties. The use of nonionic fluorosurfactants based on poly(ethylene oxide) is disclosed in U.S. Pat. Nos. 4,582,781 and 4,610,955. A typical nonionic fluorosurfactant of this kind is commercially available under the trade name Zonyl FSN and has the following linear chemical structure

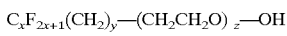

in which x varies from approximately 4 to 14 but is about 8 on average; y is 2; and z is a distribution of numbers with an average of about 10.

However, it would be an advance in the art if surfactants could be provided that were easier to dissolve in water than the nonionic fluorosurfactants typified by Zonyl FSN and yet which exhibited more surface activity or hydrophobicity.

SUMMARY OF THE INVENTION

The present invention, in one of its aspects, provides the compounds of the general formula

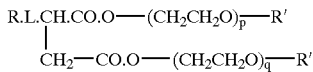

(1)

in which
R is an alkyl group with 10–20 carbon atoms, an alkenyl group with 10–20 carbon atoms or a fluoroalkyl or fluoroalkenyl group with f carbon atoms that each bear at least one fluorine atom and g carbon atoms that bear only hydrogen atoms, in which 1.5f+g=10–20 and g may optionally be zero,
R' is an alkyl group with 1 to 4 carbon atoms,
L is a linking group, a linking atom or a chemical bond, and
p is at least 2, q is at least 2 and p+q=from 4 to 100.

In another of its aspects, the present invention also provides a process for the production of an optionally substituted alkyl poly(ethylene oxide), which process comprises the steps of (1) reacting maleic anhydride with a poly(ethylene glycol) alkyl ether of the general formula

 (2)

and/or with a poly(ethylene glycol) alkyl ether of the general formula

 (3)

in which
R', p and q have the meanings stated above,
and (2) reacting the product of step (1) with a compound of the general formula

 (4)

in which
R has the meaning stated above, and
L' is a linking group or linking atom.

In a further aspect, the present invention also provides a process for the production of an optionally substituted alkyl poly(ethylene oxide) in which a compound of the general formula

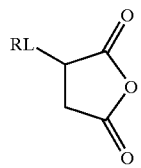 (5)

in which
R and L have the meanings stated above is reacted with a compound of the general formula

 (2)

and/or with a compound of the general formula

 (3)

in which
R', p and q have the meanings stated above.

In yet another of its aspects, the present invention further provides a photographic element comprising a substrate and a coating on the substrate, wherein the coating contains a compound of the formula (1) above or a compound that has been prepared by a process of this invention. The present invention also provides a layer of gelatin that contains a compound of the formula (1) or a compound prepared by a process of this invention.

DESCRIPTION OF EXEMPLARY EMBODIMENTS

The compounds of the present invention, which may be classified as alkyl poly(ethylene oxides), are represented by the general structure (1) given above. In that structure, R is preferably an alkyl group of the formula $C_kH_{2k+1}$, an alkenyl group of the formula $C_jH_{2j-1}$ or a fluoroalkyl group of the formula $C_nF_{2n+1}$—$(CH_2)_m$, or a corresponding fluoroalkenyl group, wherein k, j or (n+m) are equivalent to 10 to 20 carbon atoms (e.g. $CH_3$ and $CH_2$), given the premise that 1 fluorinated carbon (e.g. $CF_3$ or $CF_2$) equates to 1.5 hydrocarbon carbons. In certain preferred embodiments, R is selected from alkyl groups having from 10 to 20 carbon atoms, alkenyl groups having from 10 to 20 carbon atoms and fluoroalkyl groups of the general formula $C_nF_{2n+1}(CH_2)_m$ wherein the sum of (1.5n)+m is from 10 to 20. The definition of n and m is based on the premise that one fluorinated carbon (e.g. $CF_3$ or $CF_2$) equates to 1.5 hydrocarbon carbons (e.g. $CH_3$ or $CH_2$) in hydrophobic terms (from comparisons of critical micelle concentrations between alkyl and fluoroalkyl surfactants containing the same hydrophilic group; see E. Kissa, *Fluorinated Suactants, Surfactant Science Series*, Vol.50, Marcel Dekker (1994), 227–228). Preferably, a fluoroalkyl or fluoroalkenyl group R will be attached to the succinic acid moiety by a fluorinated carbon atom (as, for instance, when m=zero) only when L is a single chemical bond.

Although, in principle, the hydrophobic group R may be branched, it is currently preferred that R be a straight-chain group, because systems with straight hydrophobic tails are cheaper to produce. The hydrophobic group R is linked to the succinate moiety by L, which may be a linking group, such as —NH—, or linking atom, such as —S—, or simply a chemical bond, in particular a single or sigma (σ) chemical bond.

Preferably, R' denotes a methyl, ethyl, n-propyl or isopropyl group. More preferably it denotes a methyl group. The R' groups in formulae (2) and (3) may be the same or different.

In the general structure (1), p and q, which may be the same or different, may vary but preferably p+q =from 8 to 50, more preferably from 8 to 32. In certain preferred embodiments; p and q are selected so as to balance the hydrophobic group in such a manner as to produce a soluble surfactant with a low critical micelle concentration, typically of the order of $10^{-3}$M (molar) or less, preferably $10^{-4}$ M (molar) or less. In certain preferred embodiments, p and q denote the same number.

It will be appreciated, however, that the general formula (I) extends not only to individual compounds of the stated structure but also to mixtures of two or more compounds having the stated structure. In such mixtures, p and q may refer to average values.

As noted above, the compounds of the present invention may be prepared by a process in which maleic anhydride is reacted with a poly(ethylene glycol) alkyl ether, and the resultant polyethylene glycol diester of maleic acid is thereafter reacted with a compound of the general formula RL'H in which R and L' are as defined above. The reaction of the maleic anhydride with the poly(ethylene glycol) alkyl ether is generally carried out in the presence of an acid catalyst, for example sulphuric acid. The diester, which constitutes an intermediate product, may be isolated prior to further reaction. The diester intermediate product is generally reacted with the compound RL'H in the presence of a basic catalyst, for example potassium carbonate. In certain preferred embodiments, the compound of the formula RL'H is a thiol of the formula RSH, in which case the end product may be classified as an alkyl-, alkenyl-, or fluoroalkyl- or fluoroalkenyl-thiosuccinic acid, polyethylene glycol diester.

In either of the preparative processes the poly(ethylene glycol) alkyl ether may be a single compound but will usually be a mixture of such compounds having different ethoxy chain lengths. Thus the resultant product of the formula (I) will contain compounds having different chain lengths in the two ethoxy chains. It is possible to introduce the different ether groups sequentially: the first ethoxylate can be added to the anhydride to give a half ester, the remaining chain length can then be transformed into the acid chloride and the second chain can then be added under basic conditions; this may be useful if p and q are to be different. Another possibility is to fractionate a mixture of products of the formula (1).

The synthesis of fluoroalkyl, alkyl, fluoroalkenyl or alkenyl derivatives according to the first preparative process may be illustrated by the following reaction scheme (Scheme 1):

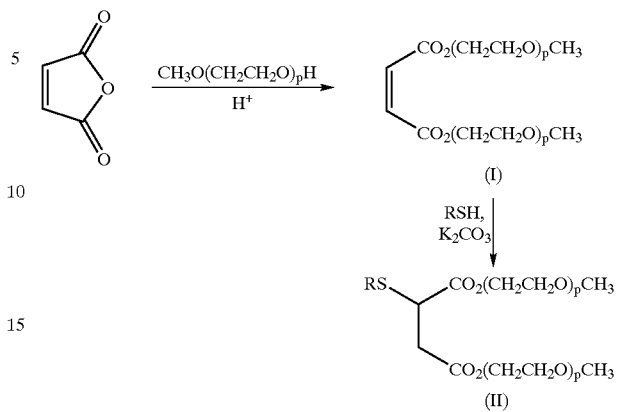

In reaction Scheme 1, p =4–16 and R has the meaning stated above in respect of formula (1), for example $C_6F_{13}CH_2CH_2$, $C_8F_{17}CH_2CH_2$ or $C_{14}H_{29}$.

Compounds according to the present invention may also be prepared, again as noted above, by a process in which an RL- substituted, e.g. an alkyl-, fluoroalkyl-, alkenyl- or fluoroalkenyl-substituted, succinic anhydride is reacted with an alkyl end-capped polyethylene glycol. This alternative preparative method provides, in particular, a way of producing compounds in which L is a single chemical bond and may be of particular interest in the production of compounds wherein R is an alkenyl group because alkenyl-substituted succinic anhydrides are commercially available in bulk. Of course, the other substituted succinic anhydrides are readily preparable by the person skilled in the art. The ethoxylated starting materials are available commercially or can be readily prepared by conventional chemical syntheses. This second preparative method may be illustrated by the following reaction scheme (Scheme 2):

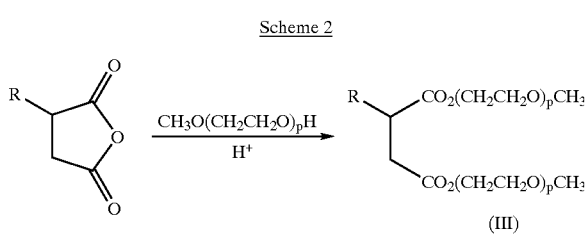

In reaction Scheme 2, R has the meaning stated above in respect of Formula (I), for example $C_{18}H_{37}$ or $C_{18}H_{35}$, and p=4–15. As indicated, the reaction is generally carried in the presence of an acid.

The compounds of the present invention, which may broadly be described as nonionic surfactants based on alkyl or alkenyl hydrophobic groups, which optionally can be at least partially fluorinated, and on two separately linked poly(ethylene oxide) hydrophilic groups, have been found to exhibit improved solubility and surface activity, compared with linearly structured poly(ethylene oxide)-based surfactants such as Zonyl FSN. Here, the notion of "improved surface activity" is understood to mean lower critical micelle concentration (CMC). Although the applicant does not wish to be bound by theory, it is believed that the improved solubility is due to the structuring of the hydrophilic group as two independently linked poly(ethylene oxide) chains, which confer a Y shape to the resulting molecule. This is believed to increase, in effect, the cross-sectional area occupied by the hydrophilic group, which encourages the formation of simple spherical micellar systems, which are easier to solubilise than systems forming rod-like or lamellar phases.

The compounds of the present invention may be used as antistatic agents in photographic products, for example coatings on substrates in photographic elements. Thus, the compounds of the invention have been found to be particularly useful for promoting surface conductivity in dried coated layers of aqueous gelatin and, as such, are useful for controlling electrostatic charging in photographic products. In such applications, the present invention may provide the advantages of better surface electrical conductivity and greater ease of dissolution than nonionic surfactants of simpler structure that are known and used in the art, such as the fluoroalkyl poly(ethylene oxide) compounds of linear chemical structure.

When present in a coating a fluorocarbon surfactant will tend to give rise to a negative electric charge upon impact of the coating against a stainless steel reference surface, whereas a hydrocarbon surfactant will tend to give rise to a positive charge. Such static electrical charges can be troublesome in various applications. Thus, in certain embodiments, it may prove beneficial to employ a mixture of at least one fluorocarbon compound of the present invention (e.g. one in which $R=C_nF_{2n+1}(CH_2)_m$) with at least one hydrocarbon compound of the present invention (R=alkyl or alkenyl) in order to balance out (or largely so) such triboelectric charges.

In certain embodiments, the compounds of the present invention may be used in conjunction with a low lattice energy salt, for example an inorganic tetrafluoroborate, perfluoroalkyl carboxylate, hexafluorophosphate or perfluoroalkyl sulphonate. Preferred are alkali metal tetrafluoroborates, trifluoroacetates, perfluorobutanoates, hexafluorophosphates, perfluorobutanesulphonates and trifluoromethanesulphonates. Such salts are discussed in U.S. Pat. No. 4,610,955 (Chen et al) and U.S. Pat. No. 4,582,781 (Chen et al), whose teaching is incorporated herein by reference. In certain especially preferred embodiments, the salt is an alkali metal triflate, in particular lithium triflate, $CF_3SO_3Li$.

EXAMPLES

The present invention is illustrated in and by the following examples. The references "I" "II" and "III" refer, respectively, to Formula I, Formula II and Formula III in the reaction Schemes 1 and 2 above.

Compounds A to E are compounds according to the present invention, of the general formula (1), in which R is an alkyl group of the formula $C_kH_{2k+1}$, an alkenyl group of the formula $C_jH_{2j-1}$ or a fluoroalkyl group of the formula $C_nF_{2n+1}$—$(CH_2)_m$, wherein k, j or (n+m) are equivalent to 10 to 20 carbon atoms (e.g. $CH_3$ and $CH_2$), given the premise that 1 fluorinated carbon (e.g. $CF_3$ or $CF_2$) equates to 1.5 hydrocarbon carbons, each R' denotes methyl, and the variables have the following values.

TABLE I

| | |
|---|---|
| A: | n = 6, m = 2, L = —S—, and p = q = 7. |
| B: | n = 8, m = 2, L = —S—, and p = q = 12. |
| C: | k = 14, L = —S—, and p = q = 12. |

TABLE I-continued

| | |
|---|---|
| D: | k = 18, L = simple chemical bond, and p = q = 12. |
| E: | j = 18, L = simple chemical bond, and p = q = 12. |

Zonyl FSN (trade name), the chemical structure of which is described herein above, was employed for comparison purposes.

Example 1

(a) Synthesis of Maleic acid, Polyethylene glycol diester (I, p=7)

Maleic anhydride (9.81 g, 0.10 mol) and poly(ethylene glycol) methyl ether MW 350 (70.0 g, 0.20 mol) were dissolved in toluene (200 ml) in a round-bottomed flask. Concentrated sulphuric acid (0.05 ml) was added as acid catalyst and the flask equipped with a Dean and Stark water trap. The mixture was stirred and refluxed for 5 hours. Toluene was removed by evaporation on a rotary evaporator and the resulting oil redissolved in ethyl acetate (200 ml). The organic solution was then washed with saturated aqueous sodium hydrogen carbonate (300 ml). The organic layer was separated and the aqueous layer reextracted with ethyl acetate (6×300 ml). The combined organic extract was dried over anhydrous magnesium sulphate, filtered, and evaporated to give a colourless oil (I, 39.9 g, 52%). Analytical data were consistent with the proposed structure.

(b) Synthesis of Fluoroalkylthiosuccinic acid, Polyethylene glycol diester (II, $R=C_6F_{13}CH_2CH_2$, p=7)

1H, 1H, 2H, 2H-tridecafluorooctyl thiol, supplied under the trade name Foralkyl EM-6, (3.80 g, 0.01 mol) and the polyethylene glycol diester (I) (7.61 g, 0.01 mol) were heated together with stirring at 130° C. under an argon atmosphere in the presence of a catalytic amount of anhydrous potassium carbonate for 5 hours. During this time the solution went from colourless to pale brown. Thin layer chromatography using ethyl acetate eluant revealed loss of thiol (no stain with iodine) and a product with a retention factor (Rf) of 0.2. The crude product was dissolved in ethyl acetate and chromatographed on silica gel (63–200 mesh) with ethyl acetate and ethanol mixtures to give, after concentration under reduced pressure, a brownish oil (II, 9.9 g, 87%). Analytical data were consistent with the proposed structure.

Example 2

Synthesis of Alkylsuccinic acid (III, p=12, R= $C_{18}H_{37}$)

Octadecylsuccinic acid (18.53 g, 0.050 mol) and poly (ethylene glycol)methyl ether MW 750 (75.00 g, 0.10 mol) were refluxed for 70 hours under an argon atmosphere in toluene (250 ml) in the presence of p-toluene sulphonic acid hydrate (0.45 g) in a flask equipped with a Dean & Stark trap. The solution was cooled and then evaporated under reduced pressure to give a yellowish oil which formed a semi-solid on cooling. The product was dissolved in ethyl acetate (1000 ml) and washed with saturated aqueous sodium hydrogen carbonate solution (500 ml). The ethyl acetate layer was dried over magnesium sulphate, filtered and evaporated to give an oil which solidified to a buff coloured waxy solid (35.64 g, 49%). Analysis was consistent with an average ethoxylate chain length of 12 units.

Example 3

A number of surfactants were tested for their ease of dissolution in water. Furthermore, the critical micelle concentrations (CMCs) of the surfactants were determined in aqueous solution containing 7% weight/weight deionised Type IV bone gelatin. The CMCs were determined from surface tension data by estimating the break point in the plot of surface tension against log concentration (see M. J. Rosen, *Surfactants and Interfacial Phenomena,* 2nd Edition, Wiley (1989), 110). The results are summarised in Table II below.

TABLE II

Surfactants: Ease of their Dissolution in Water and their CMC in Aqueous Solution Containing 7% Wt/Wt Deionised Type IV Bone Gelatin

| Surfactant | CMC in molar terms (M) moles kg$^{-1}$ | Solubility in Water |
|---|---|---|
| Zonyl FSN (comparison) | $3 \times 10^{-4}$ M | Requires relatively long stirring time to effect complete dissolution |
| A (this invention) | $6 \times 10^{-5}$ M | Dissolves easily with gentle stirring |
| B (this invention) | $1 \times 10^{-4}$ M | Dissolves easily with gentle stirring |
| C (this invention) | $7 \times 10^{-5}$ M | Dissolves easily with gentle stirring |
| D (this invention) | $8 \times 10^{-5}$ M | Dissolves easily with gentle stirring |
| E (this invention) | $4 \times 10^{-5}$ M | Dissolves easily with gentle stirring |

It will be seen that the compounds according to the present invention are easier to dissolve in water than Zonyl FSN and yet are more surface active (or more hydrophobic) in that they exhibit CMCs that are three or more times lower than that exhibited by Zonyl FSN.

Example 4

Surface Electrical Resistivity and Impact Electrostatic Charging of Gelatin-based Coatings To compare the electrostatic charging characteristics of the materials of this invention with Zonyl FSN, the following protocol was followed. Aqueous solutions (melts), containing 7% w/w gelatin, 0.25 % bis-vinyl sulphonyl methyl ether (gelatin hardener) and surfactant (at different concentrations—with and without $CF_3SO_3Li$ at half the weight of the surfactant), were coated by hand onto 7 inch wide (17.8 cm) polyethylene terephthalate film base using a 0.005 inch (127 μm) undercut stainless steel blade. The film base, which was suitably subbed to provide good adhesion of the coatings, was held by vacuum to a flat stainless steel table thermostatted at about 17° C. The melts were held at 40° C. prior to coating. After coating, the thin layers chill set rapidly and the coatings were then hung to dry overnight under ambient conditions in a room conditioned with filtered air. The coatings were then submitted for measurements of Surface Electrical Resistivity (SER) and Impact Charging (see W. J. Bailey, U.S. Pat. No. 3,501,653) against stainless steel, both at 50% RH. Tables III and IV show the SER values obtained as a function of surfactant concentration, in the presence or absence of $CF_3SO_3Li$.

TABLE III

Log SER (Ω per Square) of Coatings at 50% RH in the Presence of $CF_3SO_3Li$ (at ½ wt of surfactant added)

| | Surfactant Concentration/Wt % | | |
|---|---|---|---|
| Surfactant | 0.15 | 0.3 | 0.6 |
| Zonyl FSN (comparison) | 11.1 | 10.3 | 9.6 |
| A (this invention) | 11.0 | 10.2 | 9.6 |
| B (this invention) | 10.4 | 9.8 | 9.0 |
| C (this invention) | 10.5 | 9.0 | 8.5 |
| D (this invention) | — | — | 8.8 |
| E (this invention) | 9.6 | 9.1 | 8.4 |

TABLE IV

Log SER (Ω per Square) of Coatings at 50% RH in Absence of $CF_3SO_3Li$

| | Surfactant Concentration/Wt % | | |
|---|---|---|---|
| Surfactant | 0.15 | 0.3 | 0.6 |
| Zonyl FSN (comparison) | 11.5 | 11.4 | 11.1 |
| A (this invention) | 10.9 | 10.8 | 10.6 |
| B (this invention) | 10.7 | 10.6 | 10.4 |
| C (this invention) | 11.4 | 11.5 | 11.0 |

In the presence of $CF_3SO_3Li$ (see Table III), it is clear that compound A, with the shorter hydrophobic tail, effectively only matches Zonyl FSN. However, on a better comparison, the tails of equivalent hydrophobicity to Zonyl FSN (compounds B and C of this invention) gave significantly lower Log SERs than Zonyl FSN, i.e. about 0.5 and 1.1 log units lower respectively at concentrations of 0.3 and 0.6 wt %. The alkyl compounds of this invention are particularly effective at reducing SER in the presence of $CF_3SO_3Li$ at these concentrations: compound E gives 15×more conductivity than Zonyl FSN. The above data also show that compounds D and E exhibited the same advantages as compound C, which is also based on a hydrocarbon tail (as distinct from the fluorocarbon tail systems), in so far as very low surface resistivities were recorded.

Table IV shows that the fluoroalkyl compounds of this invention produce lower SER in gelatin coatings than the prior art compound Zonyl FSN, without the aid of a low lattice energy salt such as $CF_3SO_3Li$. The alkyl version of this invention gave an equivalent performance to Zonyl FSN.

Further experiments were carried out in order to determine the SER of coatings prepared as described above in Example 4 and including lithium triflate at half the weight of the surfactant, the tests this time being carried out at 20% RH. It may be mentioned that tests at a lower humidity represent a tougher test for an antistat system than tests carried out at a higher humidity. The results are shown in Table V below.

TABLE V

Log SER (Ω per Square) of Coatings at 20% RH in the Presence of $CF_3SO_3Li$ (at ½ wt of surfactant added)

| | Surfactant Concentration/Wt % | | |
|---|---|---|---|
| Surfactant | 0.15 | 0.3 | 0.6 |
| Zonyl FSN (comparison) | 11.9 | 10.7 | 10.1 |
| B (this invention) | 11.5 | 10.7 | 10.1 |
| C (this invention) | 12.3 | 10.2 | 9.3 |

TABLE V-continued

Log SER (Ω per Square) of Coatings at 20% RH in the Presence of CF₃SO₃Li (at ½ wt of surfactant added)

| Surfactant | Surfactant Concentration/Wt % | | |
|---|---|---|---|
| | 0.15 | 0.3 | 0.6 |
| D (this invention) | — | — | 9.2 |
| E (this invention) | 10.1 | 9.4 | 9 |

In the presence of triflate at low humidity, the fluoroalkyl system of the invention with the fluoroalkyl tail that matches the comparison compound (Zonyl FSN) is of equal effectiveness with the comparison compound; however, the hydrocarbon systems C, D and E are far more effective at lowering SER in gelatin systems than the prior art comparison compound.

A further way of comparing the electrostatic performance of the coatings is to make impact charge measurements against a standard surface such as stainless steel, using a technique pioneered by W. J. Bailey (U.S. Pat. No. 3,501,653). This technique measures the charge on a coating after a standard impact against a circular stainless steel electrode. Tables VI and VII show the values obtained from the coatings as a function of surfactant concentration, in the presence or absence of CF₃SO₃Li respectively.

TABLE VI

Impact Charging ($\mu$Cm⁻²) of Coatings after Impact Against Stainless Steel at 50% RH in the Presence of CF₃SO₃Li (at ½ wt of surfactant added)

| Surfactant | Surfactant Concentration/Wt % | | |
|---|---|---|---|
| | 0.15 | 0.3 | 0.6 |
| Zonyl FSN (comparison) | −16 | +2 | +4 |
| A (this invention) | +2 | 0 | −2 |
| B (this invention) | +6 | 0 | 0 |
| C (this invention) | +5 | +2 | 0 |

TABLE VII

Impact Values of Coatings after Impact Against Stainless Steel at 50% RH in the Absence of CF₃SO₃Li

| Surfactant | Surfactant Concentration/Wt % | | |
|---|---|---|---|
| | 0.15 | 0.3 | 0.6 |
| Zonyl FSN (comparison) | −49 | −90 | −26 |
| Aerosol OT ™ (Cyanamid: non-PEO, non-fluorosurfactant comparison - Sodium di-2-ethylhexyl sulphosuccinate) | +162 | +160 | — |
| FT248 ™ (Bayer: non-PEO, fluorosurfactant comparison - C₈F₁₇SO₃.N[C₂H₅]₄) | −81 | — | — |
| A (this invention) | −10 | +1 | 0 |
| B (this invention) | −3 | +4 | +1 |
| C (this invention) | +17 | +18 | +11 |

Table VI shows that in the presence of a low lattice energy salt, such as CF₃SO₃Li, the compounds of this invention reduce the electrostatic charging of the gelatin coatings when impacted against stainless steel, over a wide range of concentrations. At the highest concentrations, the prior art compound Zonyl FSN is able essentially to match their performance; however at the lowest concentration of 0.15%, the compounds of the invention show significantly less charging. This may be a result of their superior surface activity, i.e. lower CMC.

In the absence of CF₃SO₃Li (see Table VII), the differences between the compounds of the invention and Zonyl FSN become more marked. In this case, the compounds of this invention produce less electrostatic charging than the prior art compound, Zonyl FSN, which charges strongly negatively. The fluoroalkyl materials of this invention perform better in this context than the alkyl material of this invention. The most likely reason for the superior performance of the fluoroalkyl compounds of this invention is due to their lower SER. In general, once Log SERs become ≧11.0, charging levels appear to reach double figures. Hence a major advantage of the fluoroalkyl compounds of this invention is that they can prevent impact charging without the need for a low lattice energy salt such as, CF₃SO₃Li, which is an expensive material.

It will, of course, be understood that the present invention has been described above purely by way of example and that modifications of detail can be made within the scope of the invention.

What is claimed is:

1. A photographic element comprising a substrate and a coating on the substrate, characterised in that the coating contains a compound of the general formula $R_{[1]} =$

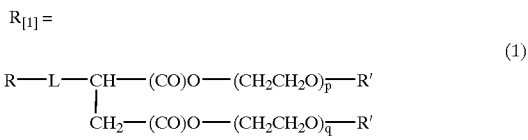

(1)

in which

R is an alkyl group with 10–20 carbon atoms, an alkenyl group with 10–20 carbon atoms or a fluoroalkyl or fluoroalkenyl group with f carbon atoms that each bear at least one fluorine atom and g carbon atoms that bear only hydrogen atoms, in which 1.5 f+g=10–20 and g may optionally be zero, R' is an alkyl group with 1 to 4 carbon atoms, L is a linking group, a linking atom or a chemical bond, and p is at least 2, q is at least 2 and p+q=from 4 to 100.

2. The photographic element according to claim 1, in which R is an alkyl group of the formula $C_kH_{2k+1}$, an alkenyl group of the formula $C_jH_{2j-1}$ or a fluoroalkyl group of the formula $C_nF_{2n+1}$—$(CH_2)_m$ wherein k, j or (n+m) are equivalent to 10 to 20 carbon atoms (CH₃ and CH₂), given the premise that 1 fluorinated carbon (CF₃ or CF₂) equates to 1.5 hydrocarbon carbons.

3. The photographic element according to claim 1, in which R is a straight-chain group.

4. The photographic element according to claim 1, in which L is selected from the group consisting of a single chemical bond, a sulphur atom and an —NH— group.

5. The photographic element according to claim 1, in which R' is a methyl group.

6. The photographic element according to claim 1, in which p+q=from 8 to 50.

7. The photographic element according to claim 1, in which p and q are selected such that the compound has a critical micelle concentration of 1×10⁻³ molar, or less.

8. The photographic element according to claim 2, in which each R' denotes methyl, n=6, m=2, L=—S—, p=7 and q=7.

9. The photographic element according to claim 2, which each R' denotes methyl, n=8, m=2, L=—S—, p=12 and q=12.

10. The photographic element according to claim 2, in which each R' denotes methyl, k=14, L=—S—, p=12 and q=12.

11. The photographic element according to claim 2, in which each R' denotes methyl, k=14, L is a single chemical bond, p=12 and q=12.

12. The photographic element according to claim 2, in which each R' denotes methyl, j=18, L is a single chemical bond, p=12 and q=12.

13. The photographic element according to claim 1 in which the coating is a gelatin coating.

14. The photographic element according to claim 1 in which the substrate is polyethylene terephthalate film base.

15. The photographic element according to claim 1 in which the coating also contains an inorganic tetrafluoroborate, perfluoroalkyl carboxylate, hexafluorophosphate or perfluoroalkyl sulphonate.

16. The photographic element according to claim 5 in which the coating contains an alkali metal triflate.

17. The photographic element according to claim 6, in which the alkali metal triflate is $CF_3SO_3Li$.

18. A compound of the general formula

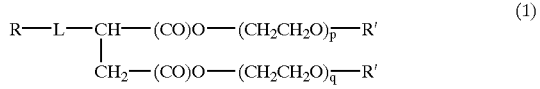

R—L—CH—(CO)O—$(CH_2CH_2O)_p$—R'|(1) $CH_2$—(CO)O$(CH_2CH_2O)_q$—R' in which

R is an alkyl group with 10–20 carbon atoms, an alkenyl group with 10–20 carbon atoms or a fluoroalkyl or fluoroalkenyl group with f carbon atoms that each bear at least one fluorine atom and g carbon atoms that bear only hydrogen atoms, in which 1.5 f+g=10–20 and g may optionally be zero, R' is an alkyl group with 1 to 4 carbon atoms, L is a linking group, a linking atom or a chemical bond, and p is at least 2, q is at least 2 and p+q =from 4 to 100.

19. The compound according to claim 18 in which R is an alkyl group of the formula $C_kH_{2j+1}$, an alkenyl group of the formula $C_jH_{2n+1}$, or a fluoroalkyl group of the formula $C_nF_{2n+1}$—$(CH_2)_m$ wherein k, j or (n+m). are equivalent to 10 to 20 carbon atoms ($CH_3$ and $CH_2$), given the premise that 1 fluorinated carbon ($CF_3$ or $CF_2$) equates to 1.5 hydrocarbon carbons.

20. The compound according to claim 19 in which R is a straight-chain group.

21. The compound according to claim 19 in which L is a single chemical bond.

22. The compound according to claim 19 in which L is a sulphur atom.

23. The compound according to claim 19 in which L is an —NH— group.

24. The compound according to claim 19 in which R' is a methyl group.

25. The compound according to claim 18 in which p+q= from 8 to 50.

26. The compound according to claim 18 in which p+q= from 8 to 32.

27. The compound according to claim 18 in which p and q are selected such that the compound has a critical micelle concentration of $1\times10^{-3}$ molar, or less.

28. The compound according to claim 19, in which each R' denotes methyl, n=6, m=2, L=—S—, p=7 and q=7.

29. The compound according to claim 19, in which each R' denotes methyl, n=8, m=2, L=—S—, p=12 and q=12.

30. The compound according to claim 19, in which each R' denotes methyl, k=14, L —S—, p=12 and q=12.

31. The compound according to claim 19, in which each R' denotes methyl, k=14, L is a single chemical bond, p=12 and q=12.

32. The compound according to claim 19, in which each R' denotes methyl, j=18, L is a single chemical bond, p=12 and q=12.

* * * * *